United States Patent [19]

Mielnik, Jr. et al.

[11] Patent Number: 4,708,849

[45] Date of Patent: Nov. 24, 1987

[54] PROCESS FOR ENERGY STORAGE AND RECOVERY

[75] Inventors: Thaddeus J. Mielnik, Jr.; Kenneth J. Fisher; Mahesh C. Aggarwal, all of Erie, Pa.

[73] Assignee: American Sterilizer Company, Erie, Pa.

[21] Appl. No.: 627,069

[22] Filed: Jul. 2, 1984

[51] Int. Cl.$^4$ .............................................. A61L 2/06
[52] U.S. Cl. ...................................... 422/26; 422/295; 422/298; 165/10; 122/406 R
[58] Field of Search ................... 422/26, 27, 38, 39, 422/295, 298, 307, 206; 62/115, 118, 119, 430, 431, 434, 439; 60/695, 659; 165/10; 122/406 R, 406 S, 406 ST

[56] References Cited

U.S. PATENT DOCUMENTS

| | | | |
|---|---|---|---|
| 3,196,631 | 7/1965 | Holland | 62/439 |
| 3,296,122 | 1/1967 | Karassik et al. | 522/26 |
| 3,977,197 | 8/1976 | Brantley, Jr. | 60/659 |
| 4,569,207 | 2/1986 | James | 62/238.6 |

*Primary Examiner*—David L. Lacey
*Attorney, Agent, or Firm*—Kirkpatrick & Lockhart

[57] ABSTRACT

A system and method for recycling first and second quantities of process heat from a vapor having substantially the total initial process heat where the vapor is channeled from at least one apparatus in which a process having a vapor utilization phase is practiced. The preferred embodiment of the system comprises at least one steam sterilizer, apparatus for channeling steam having substantially the total process heat from one of the sterilizers to a first phase change material where the first quantity of heat is absorbed by the first phase change material and water, having the second quantity of heat, is yielded. A fluid, preferably a refrigerant, is passed through the first phase change material for transfer of the first quantity of heat to the refrigerant. The refrigerant is then compressed in a compressor to provide a sufficient quantity of additional heat to raise the heat content of the refrigerant above the initial process heat. The compressed refrigerant is passed through a boiler where the first quantity of heat is transferred to water having the second quantity of heat and a sufficient quantity of additional heat is added from an additional heat source to form steam having the total process heat. The steam is selectively injected into one of the sterilizers.

6 Claims, 5 Drawing Figures

PROCESS FOR ENERGY STORAGE AND RECOVERY

BACKGROUND OF THE INVENTION

1. Field of the Invention

The present invention relates to systems for storing and recycling heat, and more particularly, to a system for, and method of, storing and recycling first and second quantities of process heat from a vapor having substantially the total initial process heat.

2. Description of the Prior Art

Conventional systems which produce heat energy for use in various apparatuses, such as steam sterilizers, washer sterilizers, and laundry and distillation equipment, generally do not consume all the heat produced for use in the processes (process heat) practiced in those apparatuses. Following the phase of the process in which the heat is utilized, the remaining, unconsumed process heat energy is cooled and vented into the atmosphere or drained.

In sterilizers, where only about 4% of the heat energy input is consumed during the process, the steam is typically exhausted from the chamber, condensed and subcooled with large volumes of water. Current plumbing codes require the temperature of drained water to be no greater than 140° F. Steam having a temperature of at least 212° F. may require in excess of three hundred gallons of water per hour to cool it to acceptable temperature levels. The large volumes of hot water cannot be recirculated in the conventional sterilizer systems. Cool water is used to pull vacuums through the piping network of steam sterilizers. Water having elevated temperatures will not effectively pull the vacuum, therefore, the water heated by the condensing steam cannot be used within the vacuum piping network and must be drained. The result is that the heat energy is lost and large volumes of water are required, providing a costly, inefficient system.

Systems for the storage of heat energy for later use have been disclosed in U.S. Pat. Nos. 3,977,197 and 4,094,148. Both of the systems described in those patents use heat energy to drive a turbine which in turn produces electricity. When the potential that initially produces the heat, produces more than can be immediately used by the system, the excess heat is stored. When the systems require more heat energy, for example during peak electricity demand hours, the stored heat energy is directed to the turbine for production of more electricity. Neither system returns the heat energy to the potential that fed the system initially. The process heat energy is not recaptured, but is stored for eventual consumption of the heat energy in the process at a later time. Neither system is adapted for use with processes that do not consume the process heat energy.

Accordingly, there is a need for a system and a method for storing and recycling the process heat energy generated for use in apparatuses which do not consume a substantial portion of that heat energy. There is a further need for such a system and a method which promotes more efficient and less costly use of all the resources associated with the system.

SUMMARY OF THE INVENTION

The present invention provides a system for use with liquids and a fluid for recycling first and second quantities of process heat from a vapor having substantially the total initial process heat for use with at least one apparatus in which a process having a vapor utilization phase is practiced.

The system includes means for channeling the vapor, preferably steam, from one of the apparatuses, preferably a steam sterilizer, and means for so absorbing the first quantity of heat, preferably the heat of vaporization, from the vapor that a first liquid, preferably water, having the second quantity of heat, preferably the sensible heat, is yielded. The absorbing means is adapted for storing the first quantity of heat. The system also includes means for so passing a fluid, preferably a refrigerant, through the first absorbing means that the first quantity of heat is substantially transferred to the fluid, means for so compressing the fluid after the fluid has substantially received the first quantity of heat that a first sufficient quantity of heat is absorbed by the fluid to raise the total heat content of the fluid above the total initial process heat, means for so tranferring the first quantity of heat from the compressed fluid and so transferring a second sufficient quantity of additional heat to liquid having substantially the second quantity of heat that vapor having the total process heat is formed, means for expanding the compressed fluid after it has transferred the first quantity of heat to the liquid in the heat transferring means, and means for selectively injecting the vapor formed in the heat transferring means into one of the apparatuses.

The system may also include a heat exchanger having a first inlet through which the first liquid having the second quantity of heat may enter, a second inlet through which a second liquid, preferably additional water, may enter, means for substantially transferring the second quantity of heat from the first liquid to the second liquid, a first outlet for draining the first liquid and a second outlet for selectively introducing the second liquid having substantially the second quantity of heat into the heat tranferring means. A pump may be used to introduce the second liquid into the heat exchanger.

Alternatively, the system may include a second means for absorbing the second quantity of heat from the first liquid, the second heat quantity absorbing means being adapted for storing the second quantity of heat, means for so passing a second liquid through the second heat quantity absorbing means that the stored second quantity of heat is substantially transferred to the second liquid, and means for selectively introducing the second liquid having substantially the second quantity of heat into the heat transferring means.

Alternatively, the system may include means for storing the first liquid having the second quantity of heat and means for selectively introducing the stored first liquid into the heat transferring means.

The system also may include means for selectively injecting the fluid, preferably air, having substantially the first quantity of heat into one of the apparatuses, means for selectively supplying additional fluid to the system, and first and second valves for activating the selective fluid supply means and delivering the fluid to said selective fluid injection means, respectively.

The heat transferring means is preferably a boiler having an additional source of heat, preferably a flash electric heater, a liquid inlet, a vapor outlet and a fluid heat exchanger for passing the compressed fluid therethrough. The boiler is adapted to receive the liquid having substantially the second quantity of heat through the liquid inlet for such combination with the second sufficient quantity of additional heat from the heat source and the first quantity of heat from the compressed fluid in the fluid heat exchanger that vapor is formed for selected injection into one of the apparatuses.

The system may include two apparatuses so associated with the system that vapor having substantially the total initial process heat from each of the apparatuses can be so channeled into the first absorbing means and vapor having the total process heat formed in the heat transferring means can be so selectively injected into each of the apparatuses that the apparatuses can share the recycled first and second quantities of process heat.

The present invention provides a process for recycling first and second quantities of process heat from the vapor having substantially the total initial process heat which includes the steps of channeling the vapor having substantially the total initial process heat from one of the apparatuses to a thermal storage unit, so absorbing the first quantity of heat from the vapor for storage in the thermal storage unit that the vapor condenses, yielding a first liquid having the second quantity of heat, selectively transferring the first quantity of heat to a fluid, so compressing the fluid after it has substantially received the first quantity of heat that the fluid absorbs a first sufficient quantity of additional heat to raise the total heat content of the fluid above the total initial process heat tranferring the first quantity of heat from the compresed fluid to liquid having substantially the second quantity of heat while transferring a second sufficient quantity of additional heat to the liquid to yield a vapor having the total process heat, expanding the compressed fluid after transfer of the first quantity of heat to the liquid and selectively injecting the vapor yield having the total process heat into one of the apparatuses.

The process may further include the steps of transferring the second quantity of heat from the first liquid to a second liquid in a heat exchanger, draining the first liquid and directing the second liquid having substantially the second quantity of heat to a boiler for heating and vapor formation. Alternatively, the process may include the steps of absorbing the second quantity of heat from the first liquid for storage in the thermal storage unit, draining the first liquid, selectively transferring the second quantity of heat to a second liquid, and directing the second liquid having substantially the second quantity of heat to a boiler for heating and vapor formation.

Alternatively, the process may include the steps of storing the first liquid having the second quantity of heat and selectively directing the first liquid having the second quantity of heat to a boiler for heating and vapor formation.

The steps of absorbing the first and second quantities of heat comprise passing the vapor through a first phase change material and passing the first liquid through a second phase change material, both disposed in the thermal storage unit, where the first and second phase change materials have such respective densities and transition temperatures that the first and second quantites of heat, respectively, are absorbed and stored therein.

The step of transferring the first quantity of heat to a fluid includes passing a fluid through the first phase change material after the first phase change material has absorbed the first quantity of heat from the vapor.

BRIEF DESCRIPTION OF THE DRAWINGS

The following detailed description of the preferred embodiment can better be understood if reference is made to the drawings in which.

DETAILED DESCRIPTION OF THE PREFERRED EMBODIMENT

FIGS. 1 through 4 illustrate the preferred embodiment of the system 10 for storing and recycling process heat from an apparatus 20 in which a process having a vapor utilization phase is practiced.

Apparatus 20 will be described in terms of a steam sterilizer for use with water. It should be appreciated, however, that other types of apparatuses which use heated vapors and liquids other than water are also within the scope of the claimed invention. Process heat is defined as the heat generated for use in the steam sterilization, or similar vapor utilization process practiced in the apparatus 20. The initial process heat is that quantity of heat actually present in the apparatus 20 during the vapor utilization phase of the process and from which the heat for storage and recycling is drawn.

Figure 1:
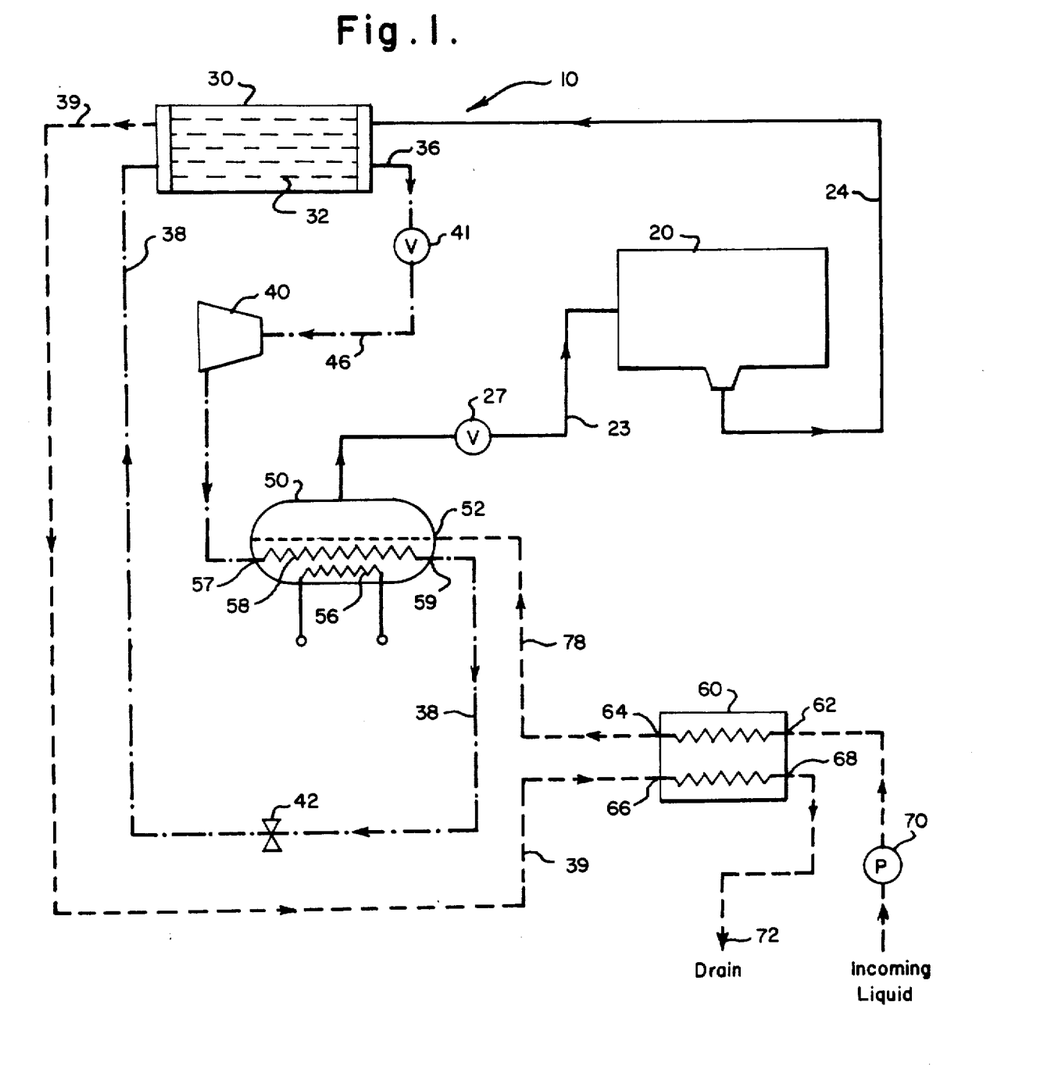
FIG. 1 is a schematic view of the preferred embodiment of the system of the present invention.

System 10 includes apparatus 20, thermal storage unit 30, compressor 40, boiler 50, liquid heat exchanger 60 and pump 70. System 10 may also include liquid reservoir 80 and alternate fluid path 48.

Figures 3, 5:
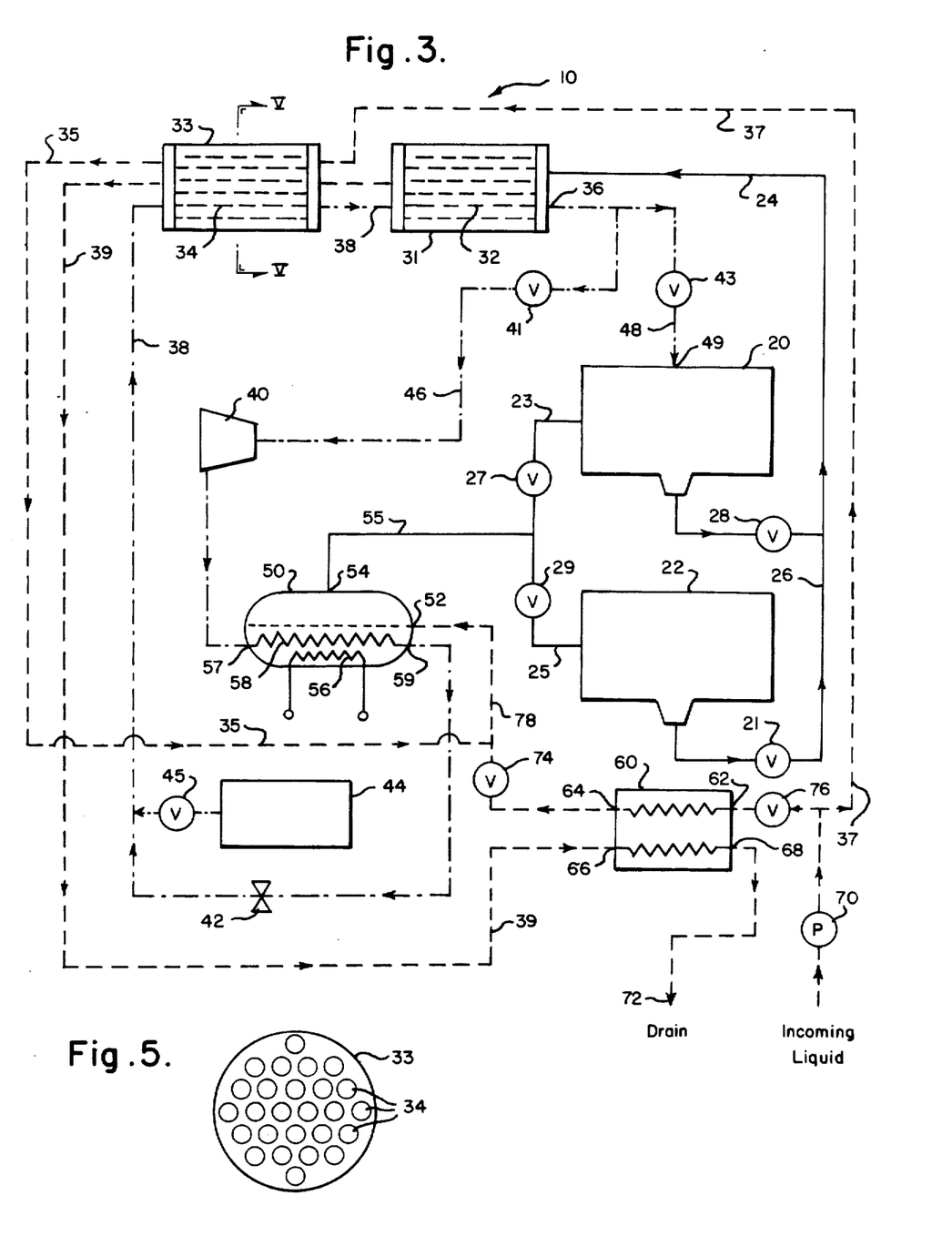
FIG. 3 is a schematic view showing an alternative embodiment of the system of FIG. 1.
FIG. 5 is a cross section view of the storage unit in FIG. 3 along the line V—V.

Thermal storage unit 30 houses phase change material (PCM) 32. PCM 32 can be any suitable known phase change material, such as a barium hydroxide salt, which has the appropriate density and transition temperature for absorbing a first quantity of heat, such as the latent heat of vaporization, from a substance with which the PCM 32 comes into thermal contact. Thermal storage unit 30 may include two units, 31 and 33. Unit 33 may house PCM 34 which can be any suitable known phase change material which has the appropriate density and transition temperature for absorbing a second quantity of heat, such as sensible heat, from a substance with which the PCM 34 comes into thermal contact. In tne preferred embodiment of the present invention, the steam from apparatus 20 passes through line 24 into the thermal storage unit 30 or 31 where it contacts PCM 32. The latent heat of vaporization of the steam, which is 9.717K Kcal/mole, is absorbed into PCM 32. The steam condenses to water having the remaining sensible heat. The hot water can be passed out of thermal storage unit 30 through line 39, or it can come into contact with PCM 34 in unit 33 which will absorb a substantial quantity of the sensible heat from the hot water. PCM 32 stores the latent heat of vaporization. PCM 34 stores a substantial quantity of the sensible heat. As the steam changes phase from a vapor to a liquid, the phase change material changes phase from a solid to a liquid. In other words, as the steam gives up its latent heat to yield water having sensible heat, the phase change material absorbs that latent heat, thereby causing the PCM to change phase as well. The choice of a phase change material is dictated by the quantity of heat it is desirable to absorb and store. A range of PCMs are commercially available. FIG. 5 illustrates a cross section of a thermal storage unit housing a PCM.

The hot water having the sensible heat passes through line 39 to inlet 66 of liquid heat exchanger 60. Incoming water, or some suitable second liquid, enters system 10, through pump 70 and inlet 62 of liquid heat exchanger 60. The sensible heat carried by the hot water condensed from the thermal storage unit 30 is substantially transferred to the incoming water in the heat exchanger 60. The cool condensate water is passed through outlet 68 to drain 72. The incoming water which now has substantially the sensible heat from the process is passed through outlet 64 to line 78 and into boiler 50 through water inlet 52.

A fluid, which may be air or a suitable refrigerant, preferably $R_{11}$ or $R_{113}$, is passed through line 38 into thermal storage unit 30 for thermal contact with the PCM 32. The latent heat of vaporization stored in PCM 32 is substantially transferred to the fluid. Because energy flows only from a higher potential to a lower potential, the fluid must be in a state to absorb the quantity of latent heat stored in the PCM 32. The refrigerant chosen is preferably one which changes phase from liquid to vapor upon passage through the thermal storage unit 30 for thermal contact with the PCM 32. As with the PCMs, the choice of fluid is dictated by the quantity of heat it is desirable to transfer.

The fluid exits the thermal storage unit 30 via line 36 and passes through valve 41 to line 46. Valve 41 can be any suitable known valve which can be selectively operated to control the passage of the fluid having substantially the latent heat of vaporization from the thermal storage unit to the compressor 40.

Compressor 40 receives the fluid through line 46 and compresses it to whatever extent is required to raise the total heat content of the fluid above the total initial process heat. The compressed fluid is passed through inlet 57 to a fluid heat exchanger 58 in boiler 50. The latent heat of vaporization carried by the fluid is transferred through a submerged coil in the boiler 50 to the water having substantially the sensible heat from the initial process heat. A sufficient quantity of additional heat is added by an electric flash heater 56, or any suitable known additional source of heat in boiler 50 to form steam, or some suitable vapor, having the total process heat. It is necessary to provide a source of additional heat to complete the steam generation step because some small quantities of heat are lost during processing through the system 10. For example, the steam sterilization process consumes about 4% of the total process heat. Additional heat may be lost by incomplete transfer to and from PCM 32 and PCM 34 or in heat exchanger 60 between the two liquids. Poorly insulated lines and storage tanks may contribute to some additional loss of heat energy to the atmosphere. In any event, some sufficient quantity of heat, though significantly less than that which would be required without the system and method provided by the present invention, must be added to complete the steam generation step. The steam is passed from boiler 50 through steam outlet 54 to line 23 and into apparatus 20 at a predetermined time when required for the steam utilization phase of the process practiced in the particular apparatus 20.

The compressed fluid passes through outlet 59 to line 38 where it is passed through an expansion valve 42. Expansion of the fluid is necessary to place it in optimum condition to absorb the latent heat of vaporization when it is again passed through the thermal storage unit 30 for contact with PCM 32. Thermal storage unit 30, PCM 32, line 36, valve 41, line 46, compressor 40, fluid heat exchanger 58, line 38 and expansion valve 42 comprise a closed loop system for recycling the latent heat of vaporization. In steam, the latent heat of vaporization constitutes about 75% of the available heat energy, thus the closed loop recycling provided by the present invention can dramatically increase the energy efficiency of a steam sterilizer.

Figure 2:
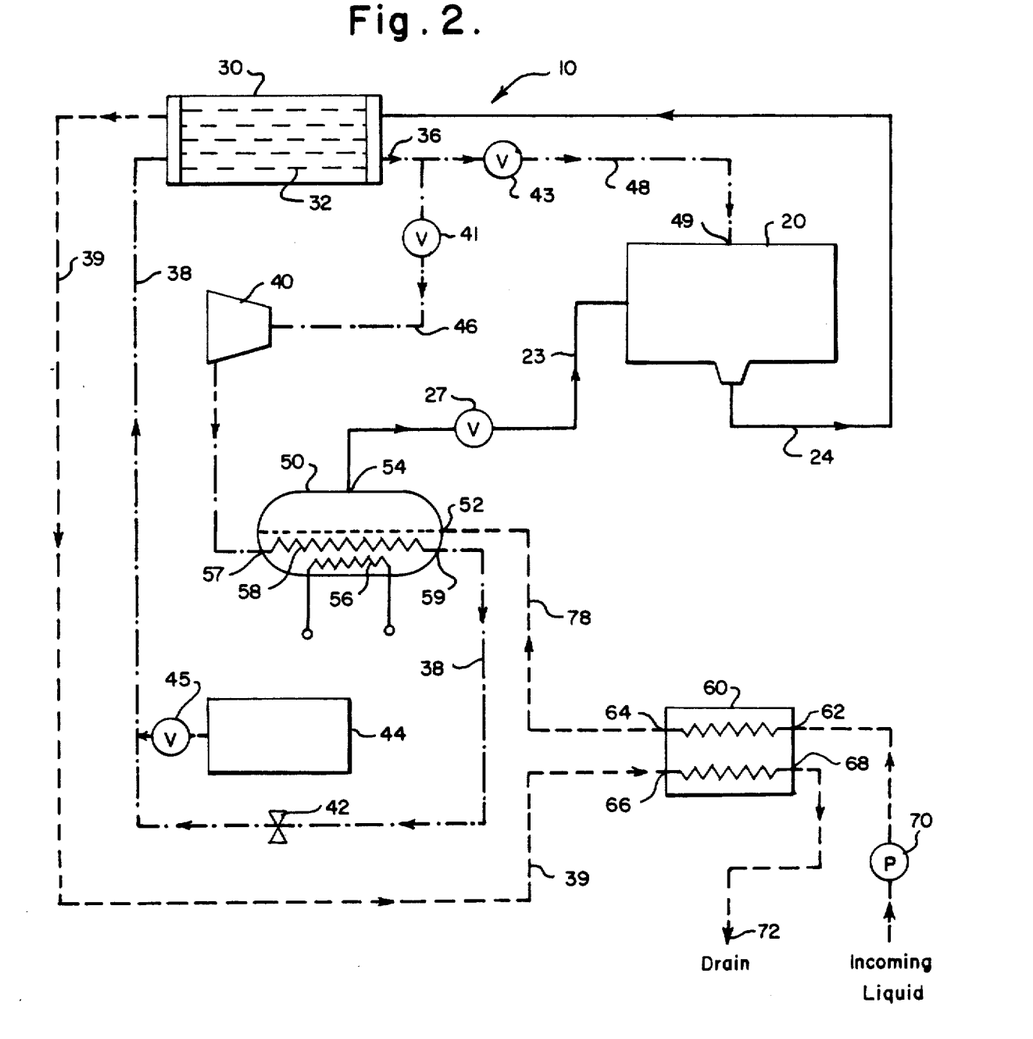
FIG. 2 is a schematic view of the system of FIG. 1 showing an alternate fluid path.

If apparatus 20 is a steam sterilizer or washer-sterilizer, a drying phase utilizing hot air may be incorporated in the process practiced in the apparatus 20. System 10 may be modified, as shown in FIG. 2 to include an alternative path for the fluid. In this embodiment, the fluid is preferably air. A valve 43 may connect line 36 to line 48 and inlet 49 into apparatus 20. The air passing through thermal storage unit 30 for thermal contact with PCM 32 absorbs the latent heat of vaporization. Valve 41 is closed and valve 43 opened. Rather than passing the hot air through compressor 40, the hot air can be diverted through valve 43 to apparatus 20. In this instance, the latent heat would not be recycled to form the steam in boiler 50. Additional fluid supply 44 and valve 45 are also included in the modification to selectively replace the fluid released from the system 10 by the diversion of the hot fluid to the alternate path.

Figure 4:
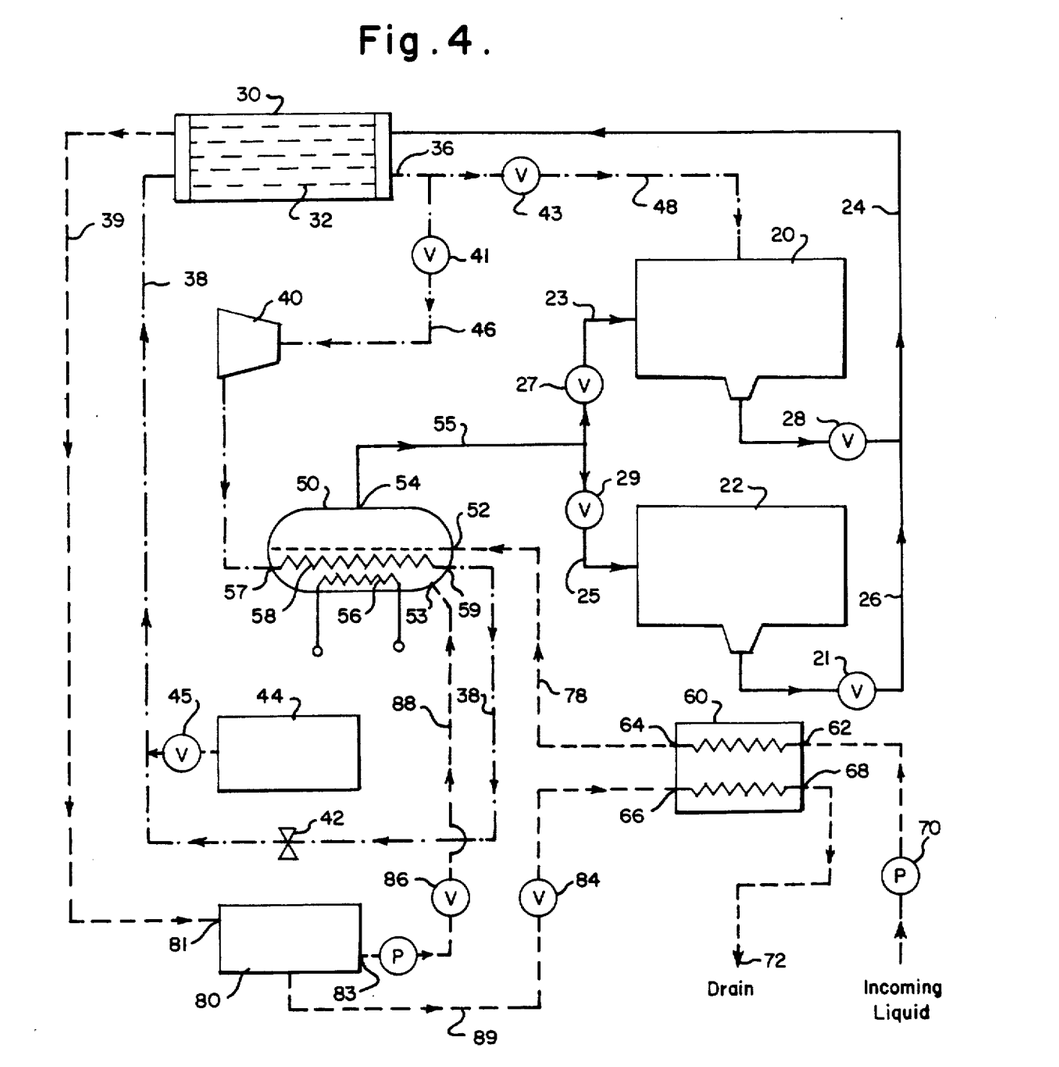
FIG. 4 is a schematic view showing a further embodiment of the system of FIG. 1.

System 10 may be utilized with at least one apparatus 20. FIGS. 3 and 4 illustrate alternative embodiments of system 10 for use with two appartuses 20 and 22. Line 55 from boiler 50 branches to lines 23 and 25. Valve 27 selectively directs steam to line 23 for use with apparatus 20. Valve 29 selectively directs steam to line 25 for use with apparatus 22. Line 26 and valve 21 selectively direct steam from apparatus 22 to thermal storage unit 30. Valve 28 selectively directs steam from apparatus 20 to line 24 and thermal storage unit 30. The alternative fluid path described above may also be directed to apparatus 22 by any suitable known means. With appropriate piping and valve arrangements, several apparatuses may be associated with system 10 to time share the heat energy stored and recycled through the system 10. Heat may be stored and ready for immediate successive use rather than having to wait for the heat to be processed through system 10 before being able to reuse apparatus 20. The storage capacity of either thermal storage unit 30 or boiler 50 or both would have to be altered appropriately in any suitable known fashion to accommodate the number of apparatuses placed on the time share modification of system 10.

System 10 may include several alternatives for handling and recycling the sensible heat from the steam. FIGS. 1 and 2 illustrate the embodiment wherein the condensation water having the sensible heat is passed through liquid heat exchanger 60. FIG. 3 illustrates an alternative embodiment which may optionally coexist with the embodiment shown in FIG. 1. Thermal storage unit 30 may include two units, 31 and 33, which house PCM 32 and 34, respectively, for absorbing and storing the latent and sensible heats, respectively. The cool condensate water would pass through line 39 to drain 72. No heat exchange would occur if heat exchanger 60. A valve 76 directs incoming water through life 37 to thermal storage unit 30 for thermal contact with PCM 34. The sensible heat is transferred to the cooler incoming water which is then passed through line 35 to line 78 for entrance through inlet 52 into boiler 50. Valve 74 on line 78 would be closed to prevent the water having substantially the sensible heat from leaving the system 10. It should be appreciated that any suitable arrangement of piping and valves can be used to pass the incoming water into thermal contact with PCM 34 for the transfer of the sensible heat and for the subsequent flow of the water to boiler 50. The condensation water, if sufficiently cooled by absorption of the sensible heat into PCM 34, can be recirculated within the sterilizer system thus, conserving water, as well as energy. The energy storage and recovery system of the present invention eliminates the large volume of water needed to cool steam condensate. A cool water recirculation system for vacuum system operation is therefore, feasible with this system.

An alternative embodiment of system 10, shown in FIG. 4, provides a reservoir 80 for storing the hot condensation water having the sensible heat after it passes from thermal storage unit 30 via line 39. The hot water passes through inlet 81 into reservoir 80. Reservoir 80 is appropriately insulated in any suitable known manner to prevent the disipation of the sensible heat through the walls of the reservoir 80. The hot condensation water having the sensible heat can be stored until needed to aid in steam formation. At the appropriate time, the hot water is pumped through outlet 83 with pump 82, through valve 86 via line 88 to inlet 53 of boiler 50. Alternatively, the hot water, or any excess hot water not pumped into boiler 50, may pass through outlet 85, trough valve 84 via line 89 to inlet 66 of heat exchanger 60, where the remaining heat may be transferred to incoming water, or may be diverted for any other hot water need. The unused hot water in reservoir 80 may also be stored there for later use in boiler 50.

System 10 may employ any suitable known heat exchanger 58 or 60, any suitable known compressor 40 or expansion valve 42, any suitable known heater 56 or boiler 50, any suitable known pumps 70 or 82, any suitable known reservoir 80, thermal storage unit 30, air supply 44 or PCMs 32 and 34. Valves 21, 27, 28, 29, 41, 43, 45, 74, 76, 84 and 86 may be any suitable known valves. In some instances a single two way or three way valve may take the place of two or three single valves disclosed in the preferred embodiment. Such alternative arrangements will be apparent from the description herein. All such suitable known equivalents for the elements of system 10 are within the scope of the claimed invention.

The method of the present invention, as practiced in system 10 described herein, includes the step of channeling the steam having substantially the total initial process heat from apparatus 20 or 22 by selective operation of valves 28 or 21, respectively, via line 24 into thermal storage unit 30 for thermal contact with PCM 32. The latent heat of vaporization is then substantially absorbed for storage by PCM 32, yielding the condensation water having the sensible heat. The latent heat is then selectively transferred to a fluid, preferably either a refrigerant or air. The fluid having the latent heat is then passed through valve 41 of line 46 for compression in compressor 40 where the fluid absorbs a sufficient quantity of additional heat due to the compression to raise the total heat content of the fluid above the total initial process heat. The compressed fluid is then passed through the fluid heat exchanger 58 in boiler 50 to transfer the latent heat from the compressed fluid to the water having substantially the sensible heat while a sufficient quantity of additional heat is added by heater 56 to aid in the formation of steam from the water in the boiler 50. The compressed fluid is passed out of boiler 50 through outlet 59 via line 38 and expanded by expansion valve 42 for subsequent use in system 10. The steam generated in boiler 50 is passed by the selective operation of valve 27 or 29 into either apparatus 20 or 22, respectively.

The method can be altered appropriately to accommodate the handling of the sensible heat in the alternative embodiments of the invention as illustrated in FIGS. 1, 3 and 4. The condensation water yielded from thermal storage unit 30 may be passed through heat exchanger 60 to transfer the sensible heat to incoming water, which then carries the sensible heat to boiler 50 for steam formation.

Alternatively, the sensible heat may be absorbed and stored in PCM 34, the cool condensation water drained and incoming water passed through thermal storage unit 33 at the desired time to receive the sensible heat from PCM 34 and carry it to the boiler 50 for steam formation.

Alternatively, the condensation water having the sensible heat may be stored in reservoir 80 until needed, then pumped via pump 82 through valve 86 into boiler 50 for steam formation.

What is claimed is:

1. In a method of using a system employing at least one liquid, a vapor and a fluid, the fluid being distinct from the at least one liquid and the vapor, and the system generating a total process heat, said system having at least one apparatus, wherein a vapor utilization phase is practiced, wherein the vapor in the at least one apparatus during the vapor utilization phase has a total initial process heat including its latent heat of vaporization and its sensible heat, the improvement including a process for recycling the latent heat of vaporization and the sensible heat from the vapor having the total initial process heat for subsequent use in the vapor utilization phase of the method, the improved process comprising:

channeling the vapor having substantially the total initial process heat from the at least one apparatus to a thermal storage unit;

absorbing the latent heat of vaporization from the vapor into a heat storing material for storage in the thermal storage unit so that the vapor condenses, yielding a first liquid having said sensible heat;

selectively transferring the latent heat of vaporization from the heat storing material to the fluid;

compressing the fluid after it has substantially received said latent heat of vaporization so that the fluid absorbs a first sufficient quantity of additional heat to raise the total heat content of the fluid above the total initial process heat;

selectively transferring said sensible heat from said first liquid to a second liquid;

transferring said latent heat of vaporization from the compressed fluid to said second liquid while transferring a second sufficient quantity of additional heat to said second liquid to yield a vapor having the total process heat;

expanding the compressed fluid after transfer of said latent heat of vaporization to said second liquid; and selectively injecting the vapor having the total process heat into the at least one apparatus for use in the vapor utilization phase of the method practiced in the at least one apparatus.

2. A method as recited in claim 1 further comprising the steps of substantially transferring the sensible heat from the first liquid to said second liquid in a heat exchanger;
   draining the first liquid; and
   directing the second liquid having substantially the sensible heat to a boiler for heating and vapor formation.

3. A method as recited in claim 1 further comprising the steps of absorbing the sensible heat from the first liquid for storage in another thermal storage unit;
   draining the first liquid;
   selectively substantially transferring the stored sensible heat to said second liquid; and
   directing the second liquid having substantially the sensible heat to a boiler for heating and vapor formation.

4. A method as recited in claim 3 wherein the step of absorbing the sensible heat comprises passing the first liquid having the sensible heat through a second phase change material disposed in said another thermal storage unit, said second phase change material having such a density and transition temperature that the sensible heat is absorbed and stored therein.

5. A method as recited in claim 1 further comprising the steps of storing the first liquid having the sensible heat and subsequently selectively directing the first liquid having the sensible heat to a boiler for heating and vapor formation.

6. A method as recited in claim 1 wherein the step of absorbing the latent heat of vaporization from the vapor comprises passing the vapor through a first phase change material disposed in the thermal storage unit, said first phase change material having such a density and transition temperature that the latent heat of vaporization is absorbed and stored therein; and
   the step of transferring the latent heat of vaporization to a fluid comprises passing the fluid through the first phase change material in the thermal storage unit after the first phase change material has absorbed the latent heat of vaporization from the vapor.

* * * * *

UNITED STATES PATENT AND TRADEMARK OFFICE
CERTIFICATE OF CORRECTION

PATENT NO. : 4,708,849

DATED : November 24, 1987

INVENTOR(S) : Thaddeus J. Mielnik, Jr. et al.

It is certified that error appears in the above-identified patent and that said Letters Patent is hereby corrected as shown below:

Col. 4, line 51, delete "tne" and substitute therefor --the--.

Col. 6, line 64, delete "if" and substitute therefor --in--.

Col. 6, line 65, delete "life" and substitute therefor --line--.

Col. 7, line 31, delete "trough" and substitute therefor --through--.

Signed and Sealed this

Fifth Day of July, 1988

Attest:

DONALD J. QUIGG

Attesting Officer

Commissioner of Patents and Trademarks